(12) United States Patent
Katti et al.

(10) Patent No.: US 6,989,158 B1
(45) Date of Patent: *Jan. 24, 2006

(54) GOLD-CONTAINING CHEMOTHERAPEUTIC AGENTS

(75) Inventors: Kattesh V. Katti, Columbia, MO (US); Wynn A. Volkert, Columbia, MO (US); Timothy Hoffman, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/019,192

(22) PCT Filed: Jun. 23, 2000

(86) PCT No.: PCT/US00/17341

§ 371 (c)(1),
(2), (4) Date: Jun. 20, 2002

(87) PCT Pub. No.: WO00/78306

PCT Pub. Date: Dec. 28, 2000

Related U.S. Application Data

(60) Provisional application No. 60/140,576, filed on Jun. 23, 1999, provisional application No. 60/156,151, filed on Sep. 27, 1999.

(51) Int. Cl.
 *A61K 31/28* (2006.01)
 *A61K 33/24* (2006.01)

(52) U.S. Cl. ..................... 424/649; 514/495

(58) Field of Classification Search ............ 514/107, 514/108, 495; 556/13, 18, 21, 110; 424/1.77, 424/604, 649
See application file for complete search history.

(56) References Cited

U.S. PATENT DOCUMENTS

| | | | | |
|---|---|---|---|---|
| 5,843,993 | A | * 12/1998 | Katti et al. | ............ 514/495 |
| 6,183,545 | B1 | * 2/2001 | Okuhama et al. | ......... 106/1.18 |
| 2002/0006915 | A1 | * 1/2002 | Strong et al. | ............... 514/44 |

OTHER PUBLICATIONS

Komiya et al, "Synthesis of water-soluble tri(hydroxymethyl)phosphine)gold(l) complexes containing a nucleoside ligand", Inorganica Chimica Acta, vol. 217, pp. 201-202 (1994).*

Chemical Abstract 127:144328, Berning et al, "Chemistry in environmentally benign media" (Sep. 2, 1997).*

Berglot, F.E., et al., "Auranofin: an Oral Chrysotherapeutic Agent for the Treatment of Rheumatoid Arthritis," *J. Rheumatol.*, 5, 68 (1978).

Berning, D.E., et al., "In Vitro and In Vivo Characterization of a $^{99m}$Tc Complex with Tris(hydroxymethyl)phosphine (THP),"Hyroxymethyl bis(phosphines) and their palladium (II) and platinum(II) complexes formed via biphasic reactions. Crystal structure of [Pd(HOH$_2$C)$_2$PC$_6$H$_4$P(CH$_2$OH)$_2$]$_2$ CL$_2$*Nucl. Med. Biol.*, 23, 617 (1996).

Fricker, S.P., "Medicinal chemistry and pharmacology of gold compounds," *Transition Met, Chem*, 21, 377 (1996).

Katti, K.V., "Recent advances in the chemistry of water-soluble phosphines—Catalytic and biomedical aspects," *Curr. Sci.*, 70, 219 (1996).

Mirabelli, C.K., et al., "Evaluation of the *In Vivo* Antitumor Activity and *In Vitro* Cytotoxic Properties of Auranofin, a Coordinated Gold Compound, in Murine Tumor Models," *Cancer Res.*, 45, 32 (1985).

Reddy, V.S., et al., "Chemistry in Environmentally Benign Media." *Inorg. Chem.*, 35, 1753 (1996).

Reddy, V.S., et al., *Inorg. Chem. Acta:*, 240; 367 (1995).

Reddy, V.S., et al., *J. Chem. Soc. Dalton Trans.*, 1301 (1996).

Schubiger, P.A., et al., "Vehicles, Chelators, and Radionuclides: Choosing the "Building Blocks" of an Effective Therapeutic Radioimmunoconjugate," *Bioconjugate Chem.*, 7, 165 (1996).

Shi, J.C., et al., Chiral Phosphine Ligands Derived from Sugars. *Inorg. Chem:*, 35, 2742 (1996).

Simon, et al, "Screening Trial with the Coordinated Gold Compound Auranofin Using Mouse Lymphocytic Leukemia P388$^1$," *Cancer Res.*, 41, 94 (1981).

Volkert, W.A., et al., "Therapeutic Radionuclides: Production and Decay Property Considerations," *J. Nucl. Med.*, 32, 174 (1991).

* cited by examiner

*Primary Examiner*—Frederick Krass
(74) *Attorney, Agent, or Firm*—Kohn & Associates, PLLC; Kenneth I. Kohn

(57) ABSTRACT

There is provided a complex for use as a therapeutic pharmaceutical, the complex has a ligand containing at least one hydroxyalkyl phosphine donor group bound to a gold atom to form a stable gold-ligand complex. Also provided is a method of treating cancer by administering an effective amount of a complex having a ligand of at least one hydroxyalkyl phosphine group bound to a gold atom to form a stable gold-ligand complex. Also provided is a method of preventing the metastasis of cancer and arresting cell growth by administering an effective amount of a complex having a ligand of at least one hydroxyalkyl phosphine group bound to a gold atom to form a stable gold-ligand complex.

3 Claims, 6 Drawing Sheets

VARIATIONS OF ALKYL CHAIN LENGTHS OF HYDROXYMETHYL PHOSPHINES

$n = 1 - 4$

GOLD-CONTAINING CHEMOTHERAPEUTIC AGENTS

CROSS REFERENCE TO RELATED APPLICATIONS

The present application is a National Phase Concerning a Filing Under 35 U.S.C. 371, claiming the benefit of priority of PCT/US00/17341, filed Jun. 23, 2000, which claims the benefit of priority of U.S. Provisional Ser. No. 60/140,576, filed Jun. 23, 1999 and U.S. Provisional Ser. No. 60/156,151, filed Sep. 27, 1999, all of which are incorporated herein by reference.

BACKGROUND OF THE INVENTION

1. Technical Field

The present invention relates to pharmaceuticals for use as therapeutic agents. More specifically, the present invention relates to pharmaceuticals containing therein gold for use as therapeutic agents.

2. Background of the Invention

Gold, in elemental form, has been employed for centuries as an antipruritic to relieve the itching palm. In more modern times, the observation by Robert Koch in 1890 that gold inhibited *Mycobacterium tuberculosis* in vitro led to trials in arthritis and lupus erythematosus, thought by some to be tuberculous manifestations. Later observations of success in treating chronic arthritis stimulated interest in gold therapy (chrysotherapy). At present, gold is employed in the treatment of rheumatoid arthritis; usually it is reserved for patients with progressive disease who do not obtain satisfactory relief from therapy with NSAIDs. However, gold compounds are among the agents that are used in an attempt to arrest the progress of the disease and to induce remissions; these are sometimes called disease-modifying drugs, although this is probably a misnomer (Edmonds et al., 1993). Since degenerative lesions do not regress once formed, there is an increasing tendency to attempt to induce remission early in the course of the disease. Such therapy is often initiated with gold, which although potentially beneficial, causes a high incidence of toxicity (Felson et al., 1992; Cash and Klippel, 1994).

Gold compounds can suppress or prevent, but not cure, experimental arthritis and synovitis due to a number of infectious and chemical agents. Gold compounds have minimal antiinflammatory effects in other circumstances and cause only a gradual reduction of the signs and symptoms of inflammation associated with rheumatoid arthritis. Although many effects of these drugs have been observed, which, if any, are related to the therapeutic effects of gold in rheumatoid arthritis is unknown. Perhaps the best hypotheses relate to the capacity of gold compounds to inhibit the maturation and function of mononuclear phagocytes and of T cells, thereby suppressing immune responsiveness. Decreased concentrations of rheumatoid factor and immunoglobulins often are observed in patients who are treated with gold.

In experimental animals, gold is sequestered in organs that are rich in mononuclear phagocytes, and it selectively accumulastes in the lysosomes of type A synovial cells and other macrophages within the inflamed synovium of patients who are treated with gold compounds. Moreover, the administration of gold thiomalate to animals depresses the migration and phagocytic activity of macrophages in inflammatory exudates, and chrysotherapy reduces the augmented phagocytic capacity of blood monocytes from patients with rheumatoid arthritis. Other mechanisms of action of gold compounds have been suggested, but none is generally accepted. These include inhibition of prostaglandin synthesis, interference with complement activation, cross-linking of collagen, and inhibition of the activity of lysosomal and other enzymes, including protein kinase C, in T cells.

Considerable research has been focused on the development of water-soluble gold-containing compounds because of their potential in medical applications [1]. The first application of gold-containing compounds came from their use in rheumatoid arthritis. The compounds used in the treatment of rheumatoid arthritis were aurothiomalate (Myocrisin) and aurothioglucose (Solgano) as depicted in FIG. 1. In 1985, another gold containing compound, auranofin, [(2,3,4,6-tetra-O-aceytl-1-thio-$\beta$-D-glucopyranosato-S)-(triethylphosphine) gold(I)] was shown to be effective for the treatment of rheumatoid arthritis [2,3]. Several studies have demonstrated that this agent is superior to the traditional chrysotherapeutic drugs. Auranofin and related gold(I) compounds have been found to be active against interperitoneal P388 leukemia and are also cytotoxic to specific tumor cells [4,5]. Mirabelli et al. screened the $\mu$-[bis(diphenylphosphino)ethane] digold complex [dppe(AuCl)$_2$] (FIG. 2) for antitumor activities [6]. Such digold complexes rearranged to give tetrahedral complexes of the type [Au(dppe)$_2$].

The tetrahedral arrangement of ligands around gold (as in Au(dppe)$_2$; FIG. 2) allowed better stabilization of the metal center through chelate effects. Such tetrahedrally-bound phosphine ligands around the gold center are more inert to substitution by potential thiolate ligands that could be encountered in a biological environment.

It was suggested that the mechanism of action for [Au(dppe)$_2$]Cl was the formation of DNA protein cross-links [7,8]. The lack of affinity of gold(I) for oxygen and nitrogen containing ligands resulted in poor reactivity with the bases of DNA.

The gold compound [Au(dppe)$_2$]Cl demonstrated marked activity against peritoneal cancer cells. However, this compound was found to be only slightly active against solid tumor models. This compound could not proceed to clinical trials due to problems with cardiotoxicity as revealed in preclinical toxicology studies [9].

Failure to identify an effective gold-containing antitumor agent stems from the difficulties associated with the development of gold compounds with optimum hydrophilicity/lipophilicity, toxicity and activity toward specific tumors. Therefore, an improved understanding of the molecular and biochemical mechanism of gold compounds can provide the impetus for new advances in the antitumor applications of gold compounds. It would also be useful to develop an antitumor gold compound which is not toxic to the patient.

It would therefore be useful to develop pharmaceuticals to develop stable non-radioactive gold complexes for use as chemotherapeutic agents.

SUMMARY OF THE INVENTION

According to the present invention, there is provided a complex for use as a therapeutic pharmaceutical, the complex including a ligand containing at least one hydroxyalkyl phosphine donor group bound to a gold atom to form a stable gold-ligand complex. Also provided is a method of treating cancer by administering an effective amount of a complex having a ligand of at least one hydroxyalkyl phosphine group bound to a gold atom to form a stable gold-ligand complex. Also provided is a method of preventing the metastasis of cancer and arresting cell growth by administering an effective amount of a complex having a ligand of at least one hydroxyalkyl phosphine group bound to a gold atom to form a stable gold-ligand complex.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
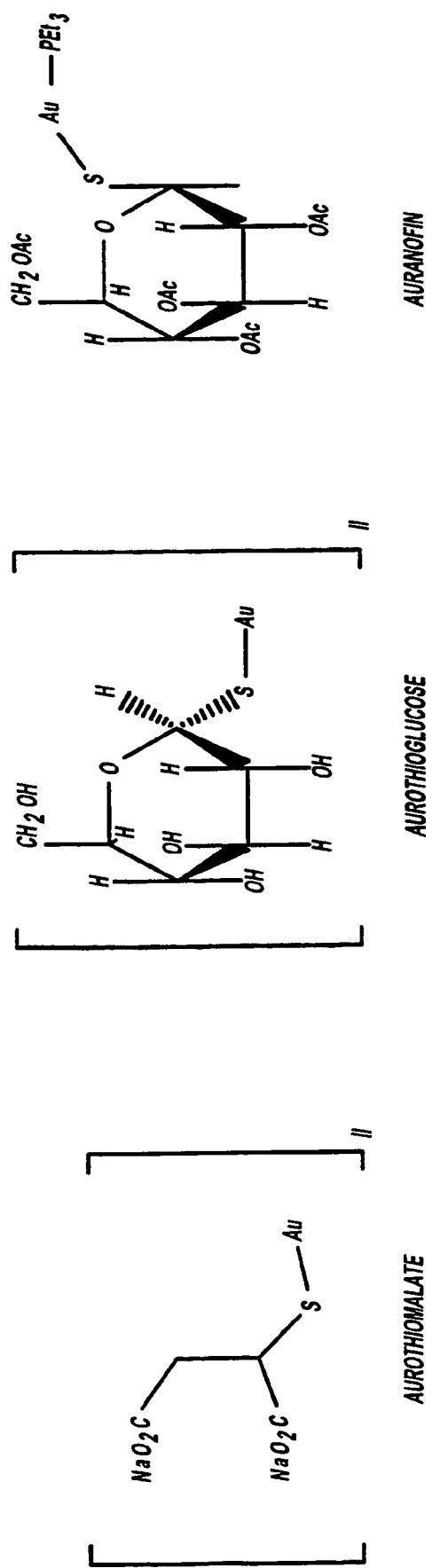
FIG. 1 illustrates the prior art gold-containing compound.
Figure 2:
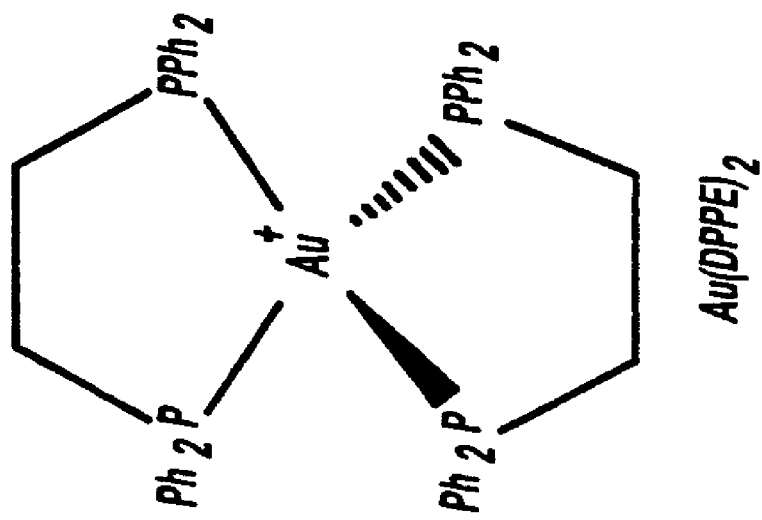
FIG. 2 illustrates further prior art gold-containing complexes.
Figure 2:
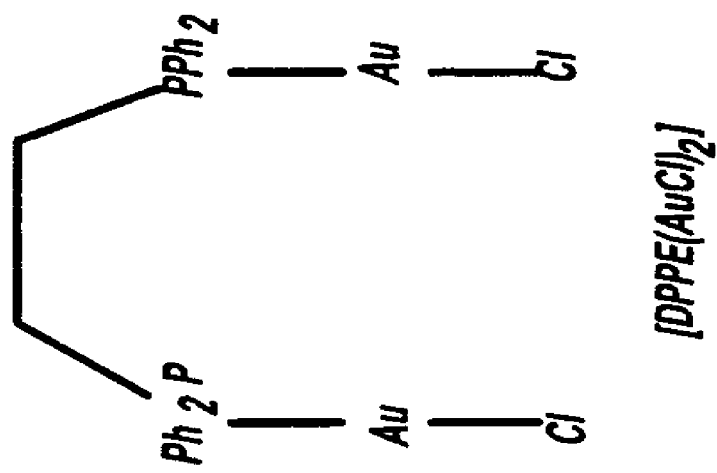
Figure 3:
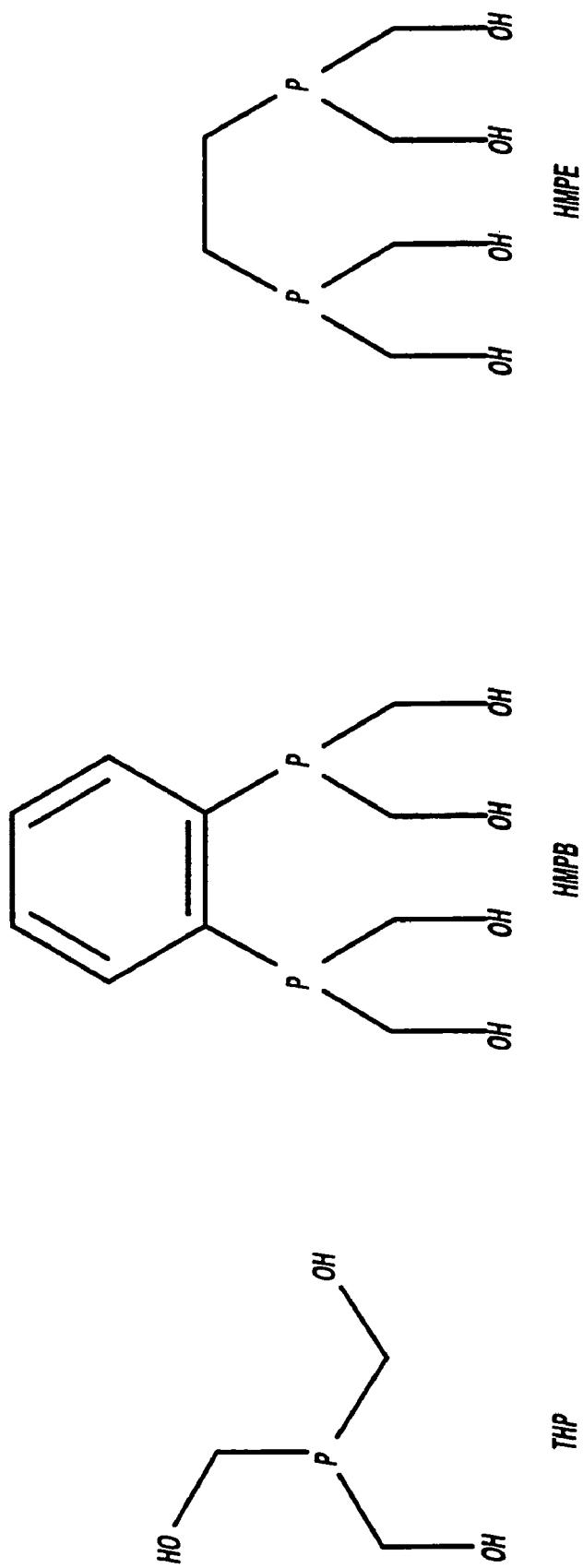
FIG. 3 illustrates representative hydroxymethyl phosphine (HMP ligands)

Generally, the present invention provides a complex for use as a therapeutic pharmaceutical. The complex includes a ligand including at least one hydroxyalkyl phosphine donor group bound to a non-radioactive gold atom to form a gold ligand complex that is stable. That is, the invention provides a ligand system containing at least one hydroxyalkyl phosphine donor group for use in forming complexes with non-radioactive gold metals wherein the complexes have high in vitro and/or in vivo stability.

The phosphorous ligands were chosen since the phosphorous atom provides a plethora of electron density that promotes formation of highly stable ligand metal bonds. This can occur even with non-radioactive gold metal in its higher oxidation states.

The hydroxyalkyl phosphine ligand is complexed with a non-radioactive gold metal, generally a gold (I) compound. These complexes contain a ratio of ligand-to-gold that is greater than or equal to 1:1 which makes the resulting chelates small and well-defined.

A complex according to the present invention can include a complex of the formula

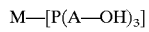

wherein M is non-radioactive gold metal in a reduced oxidation state, n is 1–6, and A is an alkyl group. In a preferred embodiment of the present invention, A is —CH$_2$—. Additionally, A can include —C$_2$H$_4$— and iso- or normal-C$_3$H$_6$—.

The non-radioactive gold-ligand complexes can include other donor atoms or groups on the same ligand as the donor hydroxyalkyl phosphine group. These other donor groups can include N, S, O, or P atoms for coordinating the non-radioactive gold atom. In addition, the donor groups can further include amines, amides, thiols, carboxyls, and hydroxyls for coordinating the non-radioactive gold atom.

In another preferred embodiment of the present invention, the complexes can include a bidentate ligand of the formula

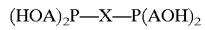

wherein A is —CH$_2$—, —C$_2$H$_4$—, or iso- or normal-C$_3$H$_6$, and X is —(CH$_2$)$_n$— where n=1–4, —CH$_2$CHR—, —CH$_2$CHRCH$_2$—, —CHRCH$_2$CH$_2$—, R'-aromatic where R' is H, an alkyl group of C$_1$–C$_4$, an aromatic group, —OH, —SH, —NH$_2$, —COOH, activated esters, N-hydroxysuccinimides, benzyl isothiocyanate, alkyl halides, or cyclohexyldiimide. Specific examples of bidentate ligands used to complex with gold can include 1,2-bis (bis(hydroxymethyl) phosphino)benzene (HMPB, 1) and 1,2-bis(bis(hydroxymethyl)phosphino)ethane (HMPE, 2) as set forth below. The formation of non-radioactive gold complexes according to the present invention with the ligands HMPB and HMPE are shown.

In further preferred embodiments, complexes according to the present invention are contemplated which include multidentate ligands of the formula

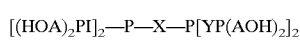

wherein A is —CH$_2$—, —C$_2$H$_4$—, or iso- or normal-C$_3$H$_6$—, and X is —(CH$_2$)$_n$-where n=1–4, —CH$_2$CHR—, —CH$_2$CHRCH$_2$—, —CHRCH$_2$CH$_2$—, or R'-aromatic where R' is H, an alkyl group of C$_1$–C$_4$, an aromatic group, —OH, —SH, —NH$_2$, —COOH, activated esters, N-hydroxysuccinimides, benzyl isothiocyanate, alkyl halides, or cyclohexyldiimide, and Y is CH$_2$—, —C$_2$H$_4$— or —C$_3$H$_6$—. Along the lines of this embodiment, further embodiments can exist wherein all of the donor atoms can be phosphorous atoms. Additionally, embodiments are contemplated wherein at least one donor group is a hydroxyalkyl phosphine group.

Furthermore, complexes according to the present invention are contemplated wherein two donor atoms are hydroxyalkyl phosphine phosphorous-atoms and two donor atoms are atoms other than phosphorous-atoms. These complexes have the general formula

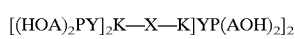

wherein A is —CH$_2$—, —(CH$_2$)$_2$—, or iso- or normal-C$_3$H$_6$—, K includes donor atoms or groups selected from the group consisting of —N—, —N(R)$^+$—, —N(H)—, Ag, and —S—, Y is —CH$_2$—, —(CH$_2$)$_2$—, or iso- or normal —C$_3$H$_6$ X is —CH$_2$—, —(CH$_2$)$_2$—, —(CH$_2$)$_3$—, —(CH$_2$)$_4$—, —CH$_2$CHR—, —CH$_2$CHRCH$_2$—, —CHRCH$_2$CH$_2$—, or R'-aromatic wherein R' and R can be the same or different and are selected from H, —OH, —SH, —NH$_2$, —COOH, activated esters, N-hydroxysuccinimides, benzyl isothiocyanate, alkyl halides, and cyclohexydiimide.

A variant of this embodiment can include a complex wherein two donor atoms are hydroxyalkyl phosphine phosphorous-atoms and two donor atoms are nitrogen-atoms (P2N2). These complexes can have the general formula

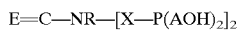

wherein X is —CH$_2$, —(CH$_2$)$_2$—, —C$_3$H$_6$—, A is —CH$_2$—, —(CH$_2$)$_2$—, —C$_3$H$_6$—, E is O or S. R can be the same or different and is selected from H, —OH, —SH, —NH$_2$, —COOH, activated esters, N-hydroxysuccinimides, benzyl isothiocyanate, alkyl halides, or cyclohexyl diimide. N is nitrogen, and Y is —CH$_2$—, —(CH$_2$)$_2$—, or iso- or norman-C$_3$H$_8$.

An additional embodiment is contemplated wherein two donor atoms are hydroxyalkyl phosphine phosphorous-atoms and two donor atoms are sulfur-atoms (P2S2).

Complexes contemplated under this embodiment have the general formula

E=C—SR—[X—P)AOH)$_2$]$_2$

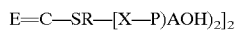

wherein X is —CH$_2$—, —(CH$_2$)$_2$—, —C$_3$H$_6$—, A is —CH$_2$—, —(CH$_2$)$_2$—, —C$_3$H$_6$—, E is O or S. R can be the same or different and is selected from H, —OH, —SH, —NH$_2$, —COOH, activated esters, N-hydroxysuccinimides, benzyl isothiocyanate, alkyl halides, or cyclohexyldiimide, S is sulfur, and Y is —CH$_2$—, —(CH$_2$)$_2$—, or iso- or normal-C$_3$H$_6$—.

A "therapeutically effective amount" is an amount of a complex of the present invention that, when administered to a patient, ameliorates a symptom of the specific disease or condition being treated. A therapeutically effective amount of a complex of the present invention can easily be determined by one skilled in the art by administering a quantity of a complex to a patient and observing the result. In addition, those skilled in the art are familiar with identifying patients having the particular disease or condition and are readily able to identify patients who suffer from these diseases or conditions.

The complexes of the present invention can be administered to a patient alone or as part of a composition that contains other components such as excipients, diluents, and carriers, all of which are well-known in the art. The compositions can be administered to humans and animals either orally, rectally, parenterally (intravenous, by intramuscularly or subcutaneously), intracisternally, intravaginally, intraperitoneally, intravescially, locally (powders, ointments or drops), or as a buccal or nasal spray.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluiditiy can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be ensured by various antibacterial and antifungal agents, for example, parbens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active complex is admixed with at least one customary inert excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin; (f) absorption accelerators, as for example, quaternary ammonium complexes; (g) wetting agents, as for example, acetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, capsules, pills, and granules can be prepared with coatings and shells, such as enteric coatings and others well-known in the art. They may contain pacifying agents and can also be of such composition that they release the active complex or complexes in a certain part of the intestinal tract in a delayed manner. Examples of embedding compositions which can be used are polymeric substances and waxes. The active complexes can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active complexes, the liquid dosage forms can contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1.3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active complexes, can contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the complexes of the present invention with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a complex of this invention include ointments, powders, sprays and inhalants. The active component is admixed under sterile conditions with a physiologically acceptable carrier and any preservative, buffers, or propellants as may be required. Ophthalmic formulations, eye ointments, powders, and solutions are also contemplated as being within the scope of this invention.

The complexes and/or compositions of the present invention can be administered to a patient at dosage levels in the range of about 0.1 to about 1,000 mg per day. For a normal human adult having a body weight of about 70 kilograms, a dosage in the range of about 0.01 to about 7000 mg per kilogram of body weight per day is sufficient. The specific dosage used, however, can vary. For example, the dosage can depend on a number of factors including the requirements of the patient, the severity of the condition being treated, and the pharmacological activity of the complex being used. The determination of optimum dosages for a particular patient is well-known to those skilled in the art.

In addition, the complexes of the present invention can exist in unsolvated as well as solvated forms with pharmaceutically acceptable solvents such as water, ethanol, and the like. In general, the solvated forms are considered equivalent to the unsolvated forms for the purposes of the present invention.

The complex of the present invention can be coadministered with an additional therapeutic agent. This therapeutic can include, but is not limited to, chemotherapeutic agents. Preferably, the complex of the present invention and the coadministered therapeutic agent work in conjunction with on another to create a more sustained effect. These two therapeutic agents can be either administered in one pharmaceutically acceptable carrier or separately.

Figure 4:
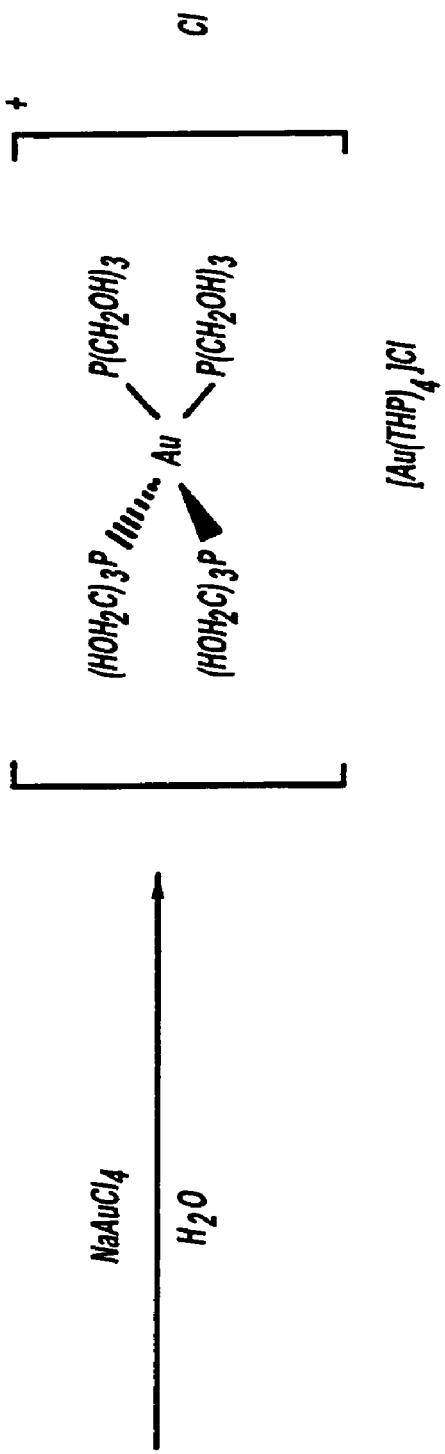
FIG. 4 illustrates the synthesis of trihydroxymethyl phosphine gold complexes.

When the non-radioactive analogue of the gold complex of THP [(Au(THP)$_4$)] (FIG. 4) was tested for tumor cell suppression against specific human cancer cells lines, it came as a total surprise that this compound exhibited remarkable activity in suppressing tumor growth in in vitro conditions. The data for 50% and 70% tumor growth suppression of cells derived from human colon carcinoma are summarized in Tables 1 and 2.

The data in Table 1 demonstrates that 50% tumor growth suppression occurs at ~2 $\mu$g of the gold compound. This invention is significant in that it demonstrates high efficacy of tumor growth suppression under extremely low doses of the new antitumor agent (Au(THP)$_4$]Cl. The tumor growth suppression for cells derived from human gastric carcinoma have been tested. The data for 50% and 70% tumor growth suppression are summarized in Tables 2 and 4 respectively. This 50% tumor growth suppression of cells derived from human gastric carcinoma occurs at about 10 mg of [Au (THP)$_4$]Cl. This is the first demonstration that hydroxymethyl phosphine (HMP)-bound gold compounds display high efficacy in suppressing tumor growth of specific cells derived from human carcinoma.

Clinically, cisplatin is widely used as a chemotherapeutic agent in the treatment of human cancer. Use of cisplatin is generally associated with severe toxic side effects that include decrease in blood cell numbers, kidney dysfunction, etc. Therefore, cisplatin cannot be used in treating cancer patients for longer periods of time. Gold-containing compounds are less toxic and their non-toxic dose is generally higher than that of cisplatin. Therefore, it is practical to treat cancer patients using gold-containing chemotherapeutic agents for longer durations. In this context, the tumor growth suppression data reported for [Au(THP)$_4$]Cl demonstrates the potential of using this (and related) now generation of gold-containing compounds in treating cancer bearing patients.

The above discussion provides a factual basis for the use of gold-containing chemotherapeutic agents. The methods used with and the utility of the present invention can be shown by the following non-limiting examples and accompanying figures.

EXAMPLES

Example 1

Histogram Studies:

Histogram studies were carried out using HCT-15 cells. In the enclosed figure that summarize histogram results the cells are numbered as follows: HCT-80 is the control; HCT-81 refers to a sample with 200 $\mu$g/ml of the gold compound; HCT-82 refers to a sample with 40 $\mu$g/ml of gold compound.

HCT-15 cells were incubated in 5% $CO_2$ incubator for two days. Then the cells were harvested and analyzed using fluorescent techniques. As shown on the enclosed figures, the percent of G1 phase in the cell cycle is significantly less for the control as compared to the cell samples that contained 200 or 40 $\mu$g of gold compound. This is an important finding because it clearly demonstrates that the gold compound elongates G1 phase and consequently slows cell growth. This finding is in sharp contrast to he cytotoxic side effects of cisplatin which is known to cause disassociation of many phases. Additionally, most agents which are cytotoxic, block S or M+ G2 phase after culturing for two days. The mode of cell suppression via G1 phase elongation, as observed for the gold compound, therefore functions differently.

In Vivo Studies:

The data of in vivo studies are summarized in Table: In vivo below. As shown in this table, the gold compound causes remarkable survival of tumor bearing mice. Administration of gold compound in doses significantly larger than the amount shown in this table (20–25 $\mu$g/kg) did not result in deaths of tumor bearing mice. Cisplatin at such doses resulted in the death of animals.

Side Effects:

Preliminary findings, to date, have indicated no toxic cardiovascular or naphrotoxic side effects (in mice models) for the {Au[THP]$_4$Cl} compound.

TABLE

In vivo
R sults of in viv study of [Au(THP)$_4$Cl]
Male 3.5 weeks weighing 17 to 20 g. mice.
Balb/C mice inoculated 30,000 of Meth/A cells i.p. on Jun. 9, 1999

| Control mice (n = 17) date | mice administered with Au compound of 1 mg/kg s.c. for three times daily for three days only (3 mg/kg total) (n = 17) | mice administered with Au compound of 0.2 mg/kg s.c. for three times daily for three days only (0.6 mg/kg total) (n = 15) |
| --- | --- | --- |
| 6/9 0/17 | 0/17 | 0/15 |
| 6/25 1/16 | 0/17 | 0/15 |
| 6/26 1/15 | 0/17 | 0/15 |
| 6/28 1/14 | 0/17 | 0/14 |
| 6/29 1/13 | 0/17 | 0/13 |
| 6/30 0/13 | 0/17 | 0/13 |
| 7/1 0/13 | 0/17 | 0/13 |
| 7/2 3/10 | 1/16 | 1/12 |
| 7/3 2/8 | 0/16 | 1/11 |
| 7/5 0/8 | 1/15 | 0/11 |
| 7/6 0/8 | 0/15 | 1/10 |
| 7/8 0/8 | 0/15 | 0/10 |
| 7/9 0/8 | 0/15 | 0/10 |
| 7/10 0/8 | 0/15 | 0/10 |
| 7/14 0/8 | 0/15 | 0/10 |
| 7/20 0/2 | 0/15 | 0/10 | a/b: a = number of dead mice b = number of living mice

Figure 5:
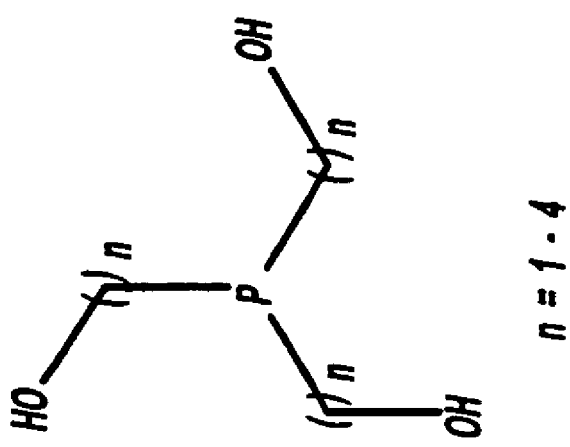
FIG. 5 illustrates variations of alkyl chain length of hydroxymethyl phosphines.
Figure 6:
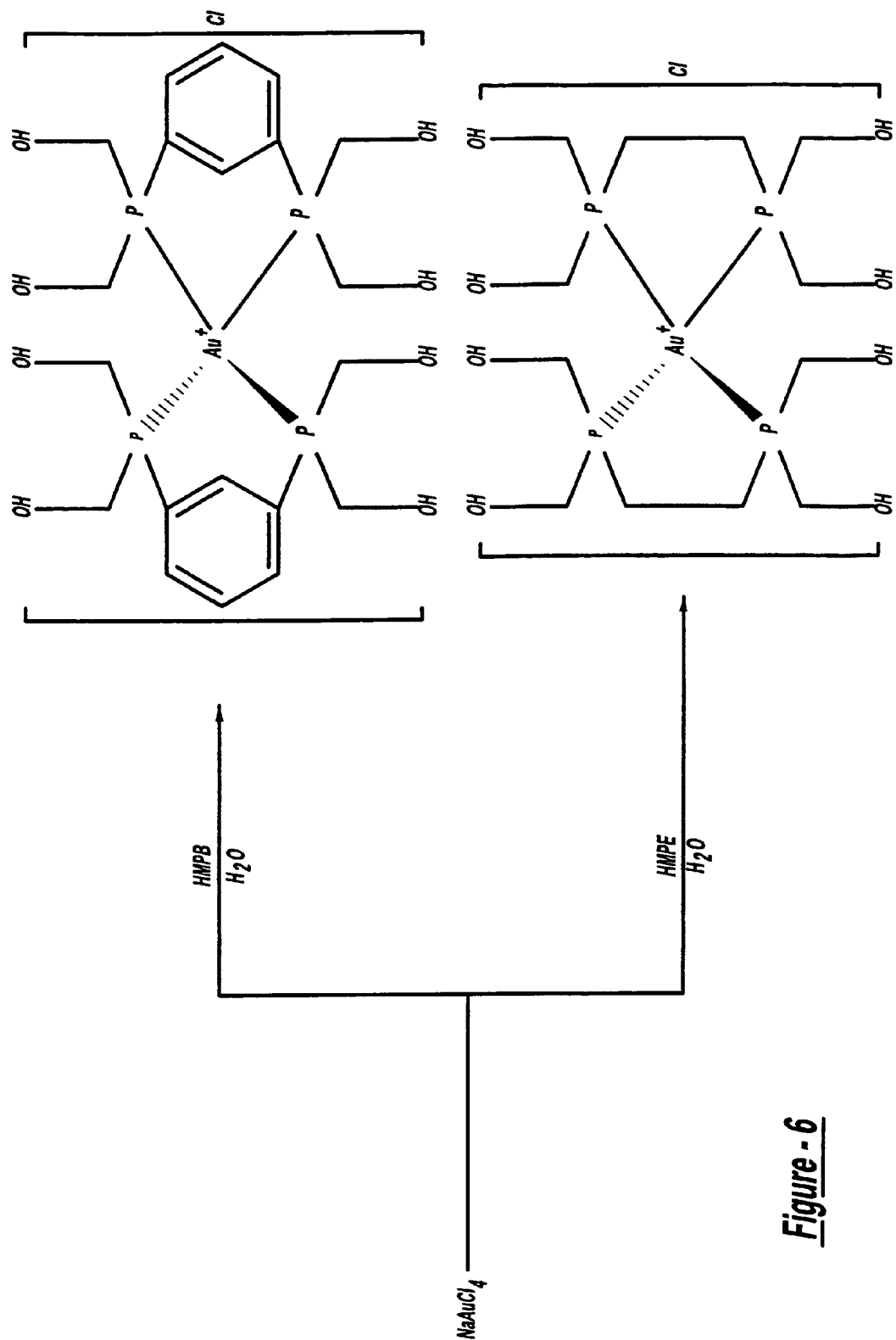
FIG. 6 illustrates alternative approaches of chelating HMP groups to produce tetrahedral gold compounds.

The data summarized in Tables 1–4 demonstrate the efficacy of [Au(THP)$_4$]Cl in suppressing tumor growth of human colon cancer and human gastrin cancer cells. This compound is effective in treating various other carcinoma such as prostate cancer, breast cancer, brain tumors and also pancreatic cancer. The pharmacokinetic and drug action of Au-containing chemotherapeutic agents can be readily altered by systematic modifications of HMP ligands. One way is to vary the alkyl chains of alkyl hydroxy groups as shown in FIG. 5. The other approach would involve utility of chelating HMP compounds such as HMPB and HMPE to produce tetrahedral gold compounds as shown in FIG. 6. Therefore, chemical modifications of ligand backbones allows systematic tuning of gold pharmacophore characteristics. This aspect is important in terms of the design and development of gold-contasining chemotherapeutic agents with optimum hypophilic/liphophilic characteristics and charge on the gold center that may be needed in the treatment of specific human carcinoma.

Potential applications of [Au(THP)$_4$]Cl and related analogues include (but are not limited to): (i) treatment of small cell lung cancer; (ii) treatment of prostate cancer; (iii) treatment of breast, colon, pancreatic cancers and other kinds of malignancies; and (iv) treatment of rheumatoid arthritis.

Throughout this application, various publications, are referenced by author and year. Full citations for the publications are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

1. Kamei, H.; Koide, T.; Kojima, T.; Hashimoto, Y.; Hasegawa, M. Cancer Biotherapy & Radiopharmaceuticlas. 1998, 13, 403.
2. Fricker, S. P. Transition Met. Chem. 1996, 21, 377.
3. Berglof, F. E.; Berglof, K.; Walz, D. T. J. Rheumatol. 1978, 5, 68.
4. Simon, T. M.; Kunishima, D. H.; Vibert, G. J.; Lorber, A. Cancer Res. 1981, 41, 94.
5. Mirabelli, C. K.; Johnson, R. K.; Sung, C. M.; Faucette, L.; Muirhead, K.; Crooke, S. T. Cancer Res. 1985, 45, 32.
6. Snyder, R. M.; Mirabelli, C. K.; Johnson, R. K.; et al. Cancer Res. 1986, 46, 5064.
7. Berners, S. J.; Jarrell, P. S.; Sadler, P. J. Inorg. Chem. 1987, 26, 3074.
8. Sadler, P. Agnew, Chem. Int. Ed. 1999, 38, 1512.
9. Hoke, G. D.; Macia, R. A.; Meunier, P. J.; Bugelski, P. J.; Mirabelli, C. K.; Rush, G. F.; Matthews, W. D. Toxicol. Appl. Pharmacol. 1989, 100, 293.
10. Volkert, W. A.; Goeckeler, W. F.; Ehrhardt, G. J.; Ketring, A. R. J. Nucl. Med. 1991, 32, 174.
11. Schubiger, P. A.; Alberto, R.; smith, A. Bioconjugate Chem. 1996, 7, 165.
12. Shi, J. C.; Huang, X. Y.; Wu, D. X.; Liu, Q. T.; Kang, B. S. Inorg. Chem. 1996, 35, 2742.
13. Rush, G. F.; Alberts, D. W.; Meunier, D.; Leffler, K.; Smith, P. F. Toxicologist 1987, 7, 59.
14. Katti, K. V. Curr. Sci. 1996, 70, 219.
15. (a) Reddy, V. S.; Berning, D. E.; Katti, K. V.; Barnes, C. L.; Volkert, W. A.; Ketring, A. R. Inorg. Chem. 1996, 35, 1753. (b) Reddy, V. S.; Katti, K. V.; Barnes, C. L. J. Chem. Soc. Dalton Trans. 1996, 1301. (c) Reddy, V. S.; Katti, K. V.; Barnes, C. L. Inorg. Chem. Acta. 1995, 240, 367.
16. Berning, D. E.; Katti, K. V.; Sing; P. R.; Kiggenbotham, C.; Reddy, V. S.; Volkert, W. A. Nucl. Med. Biol. 1996, 23, 617.
17. Smith, C. J.; Katti, K. V. et al. Nucl. Med. Biol. 1997, 24, 685.
18. Berning, D. E.; Katti, K. V. et al. Nucl. Med. Biol. 1998, 25, 577.

What is claimed is:

1. A method of treating prostate, colon, or gastric cancer comprising
   administering, to a subject in need thereof, an effective amount of a complex comprising a ligand comprising at least one hydroxyalkyl phosphine group, which is bound to a non-radioactive gold atom to form a stable gold-ligand complex.

2. A method of inhibiting metastasis of prostate, colon, or gastric cancer comprising administering, to a subject in need thereof, an effective amount of a complex comprising a ligand comprising at least one hydroxyalkyl phosphine group which is bound to a non-radioactive gold atom to form a stable gold-ligand complex.

3. A method of reducing cell growth of prostate, colon, or gastric cancer comprising administering, to a subject in need thereof, an effective amount of a complex comprising a ligand comprising at least one hydroxyalkyl phosphine group, which is bound to a non-radioactive gold atom to form a stable gold-ligand complex.

* * * * *

UNITED STATES PATENT AND TRADEMARK OFFICE
CERTIFICATE OF CORRECTION

PATENT NO. : 6,989,158 B1  Page 1 of 1
DATED : January 24, 2006
INVENTOR(S) : Kattesh V. Katti et al.

It is certified that error appears in the above-identified patent and that said Letters Patent is hereby corrected as shown below:

<u>Column 1,</u>
Line 15, insert:
-- This invention was made with government support under Grant No. DE-FG02-89ER60875 awarded by the Department of Energy. The government has certain rights in the invention. --.

Signed and Sealed this

Twenty-fifth Day of April, 2006

JON W. DUDAS
*Director of the United States Patent and Trademark Office*